United States Patent
Lin

(10) Patent No.: US 8,408,069 B2
(45) Date of Patent: Apr. 2, 2013

(54) TORSION SPRING TEST JIG

(75) Inventor: Jui-Pin Lin, New Taipei (TW)

(73) Assignee: Cheng Uei Precision Industry Co., Ltd., New Taipei (TW)

( * ) Notice: Subject to any disclaimer, the term of this patent is extended or adjusted under 35 U.S.C. 154(b) by 224 days.

(21) Appl. No.: 13/094,813

(22) Filed: Apr. 26, 2011

(65) Prior Publication Data

US 2012/0272746 A1     Nov. 1, 2012

(51) Int. Cl.
     *G01N 3/22*        (2006.01)
(52) U.S. Cl. ............................................ 73/847; 73/161
(58) Field of Classification Search .................. 73/760, 73/847, 161
See application file for complete search history.

(56) References Cited

U.S. PATENT DOCUMENTS

| | | | | |
|---|---|---|---|---|
| 2,765,655 A | * | 10/1956 | Scott ................................ | 73/161 |
| 2,799,162 A | * | 7/1957 | Carlson ............................ | 73/161 |
| 4,686,906 A | * | 8/1987 | Meindl ............................ | 104/209 |
| 4,905,506 A | * | 3/1990 | Lebershausen ................ | 73/114.77 |
| 6,094,980 A | * | 8/2000 | Larson et al. .................... | 73/161 |
| 6,397,657 B1 | * | 6/2002 | Kroll et al. .................... | 73/11.05 |

* cited by examiner

*Primary Examiner* — Max Noori
(74) *Attorney, Agent, or Firm* — Cheng-Ju Chiang

(57) ABSTRACT

A torsion spring test jig adapted to assist a torsion spring to show different elastic statuses includes a bottom holder, a sliding element slidably mounted on the bottom holder and a plurality of hinge pin assemblies. The bottom holder includes a first modulating fastener having a first groove and a second modulating fastener having a second groove perpendicularly positioned under the first modulating fastener. An intersection of the first and second groove forms a first locating perforation. The sliding element includes a third modulating fastener having a third groove and a fourth modulating fastener having a fourth groove perpendicularly positioned under the third modulating fastener. An intersection of the third and fourth grooves forms a second locating perforation. The torsion spring are fastened between the first and second perforations through the hinge pin assemblies.

6 Claims, 6 Drawing Sheets

TORSION SPRING TEST JIG

BACKGROUND OF THE INVENTION

1. Field of the Invention

The present invention relates to a test jig, and more particularly to a torsion spring test jig.

2. The Related Art

Currently, slip cover mechanisms are widely used in electronic apparatuses, such as cell phones. The slip cover mechanism generally includes a base and a torsion spring playing an important functional effect on the slip cover mechanism. In order to test force condition and using life of the torsion spring used in the electronic apparatus, a torsion spring test jig which can simulate an assembling status of the torsion spring assembled in the electronic apparatus is needed. However, the torsion spring can only be fastened in one place of the torsion spring test jig to keep a single elastic status during a process of test. Accordingly, only a test parameter of the single status can be got from the test using the above-mentioned torsion spring test jig. In order to get parameters of other elastic statuses of the torsion spring, the torsion spring need be changed places in the torsion spring test jig, or changed different groups of the torsion spring test jigs to test different elastic statuses of the torsion spring. As a result, the manufacturing cost of the torsion spring test jig is higher, and it is complicated to test the force condition and using life of the torsion spring.

SUMMARY OF THE INVENTION

An object of the present invention is to provide a torsion spring test jig adapted to assist a torsion spring to show different elastic statuses so as to test the torsion spring under the different elastic statuses. The torsion spring test jig includes a bottom holder, a sliding element and a plurality of hinge pin assemblies. The bottom holder has a base body. The base body defines a first fastening frame. A first modulating fastener is slidably mounted between two opposite inner sidewalls of the first fastening frame, and a second modulating fastener is slidably mounted in the first fastening frame and perpendicularly positioned under the first modulating fastener. The first modulating fastener has a first groove, and the second modulating fastener has a second groove extending perpendicularly to the extension direction of the first groove. Each intersection of the first groove and the second groove forms a first locating perforation of which the position can be shifted with the relative movement between the first modulating fastener and the second modulating fastener. The sliding element has a base board. The base board defines a second fastening frame. A third modulating fastener is slidably mounted between two opposite inner sidewalls of the second fastening frame, and a fourth modulating fastener is slidably mounted in the second fastening frame and perpendicularly positioned under the third modulating fastener. The third modulating fastener defines a third groove, and the fourth modulating fastener defines a fourth groove extending perpendicularly to the extension direction of the third groove. Each intersection of the third groove and the fourth groove forms a second locating perforation of which the position can be shifted with the relative movement between the third modulating fastener and the fourth modulating fastener. The sliding element is slidably disposed over the bottom holder to achieve a relative movement between the first locating perforation and the second locating perforation. Two free ends of the torsion spring is fastened to the first perforation and the second perforation respectively by means of the hinge pin assembly to mount the torsion spring between the first and second modulating fasteners, and between the third and fourth modulating fasteners.

As described above, the torsion spring is fastened between the first and second modulating fasteners of the bottom holder and the third and fourth modulating fasteners of the sliding element of the torsion spring test jig by means of the hinge pin assemblies. The sliding element slides along the sliding grooves to drive the torsion spring to be flexibly expanded and contracted so as to show the different elastic statuses, so that different parameters of the force condition and the using life of the torsion spring can be tested. Furthermore, the modulating fasteners can be modulated to define different positions of the first and second perforations so as to meet varied needs of testing the torsion spring. So, the cost of testing the force condition and the using life of the torsion spring is lowered and test efficiency is improved.

BRIEF DESCRIPTION OF THE DRAWINGS

The present invention will be apparent to those skilled in the art by reading the following description thereof, with reference to the attached drawings, in which.

DETAILED DESCRIPTION OF THE PREFERRED EMBODIMENT

Figure 1:
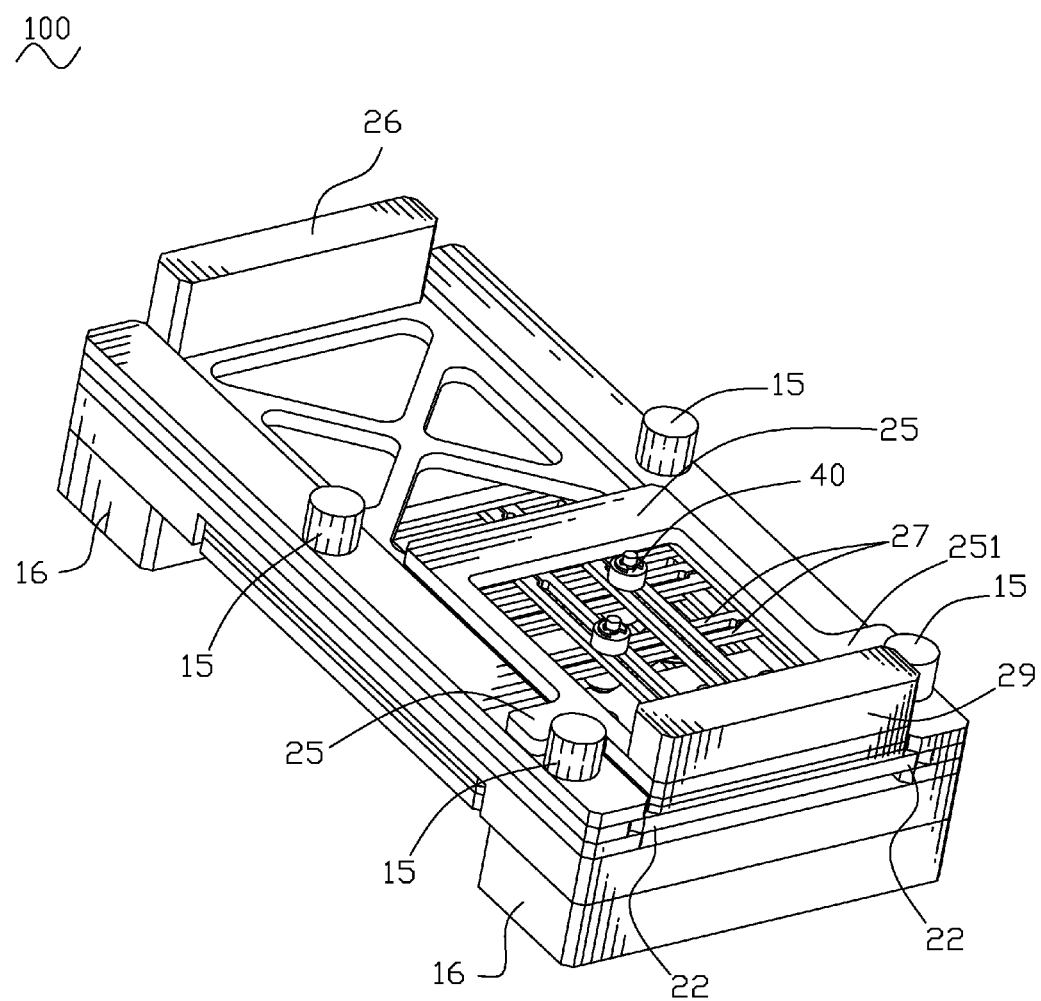
FIG. 1 is a perspective view of a torsion spring test jig according to the present invention.
Figure 2:
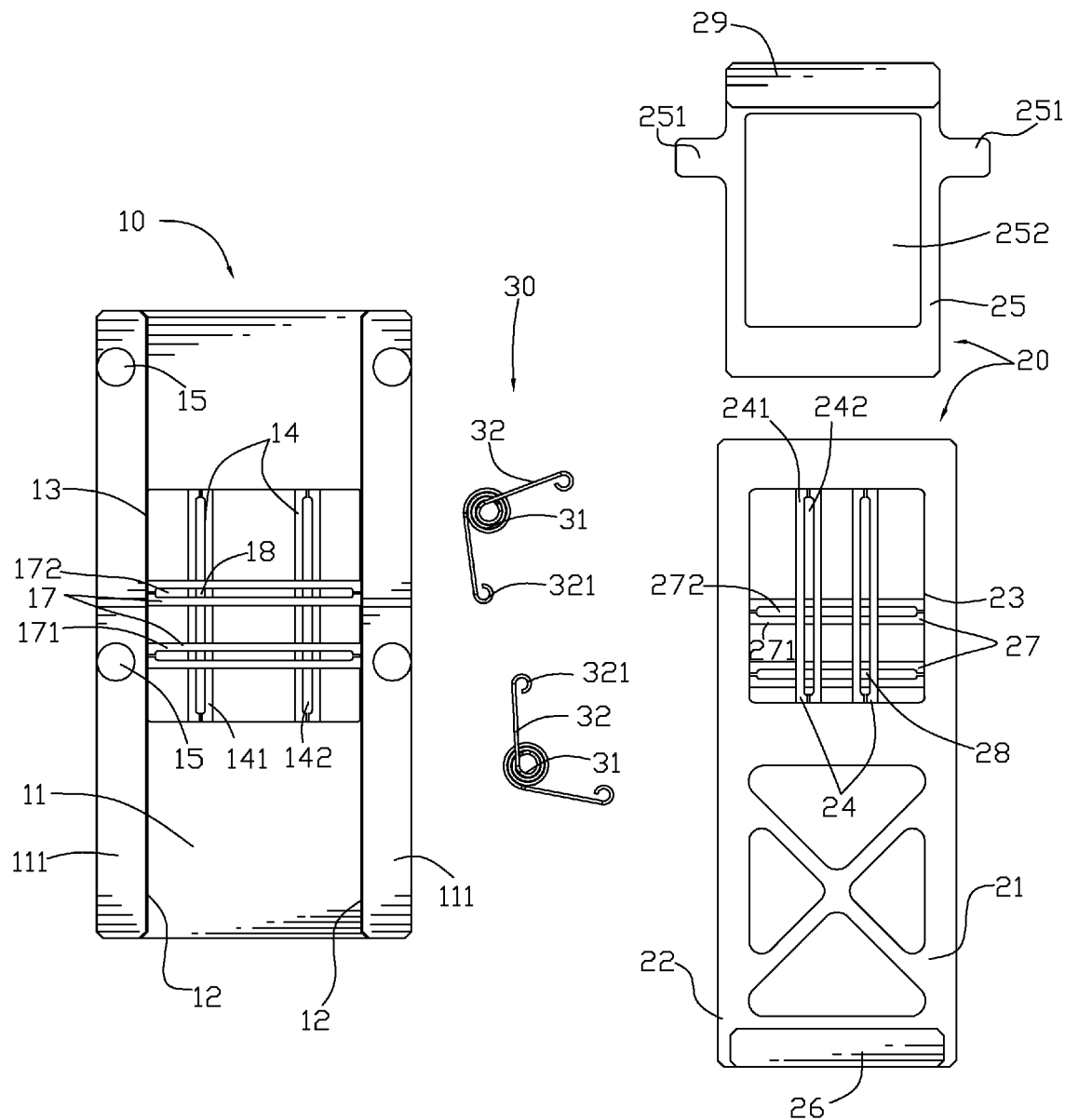
FIG. 2 is an exploded perspective view of the torsion spring test jig of FIG. 1.
Figure 3:
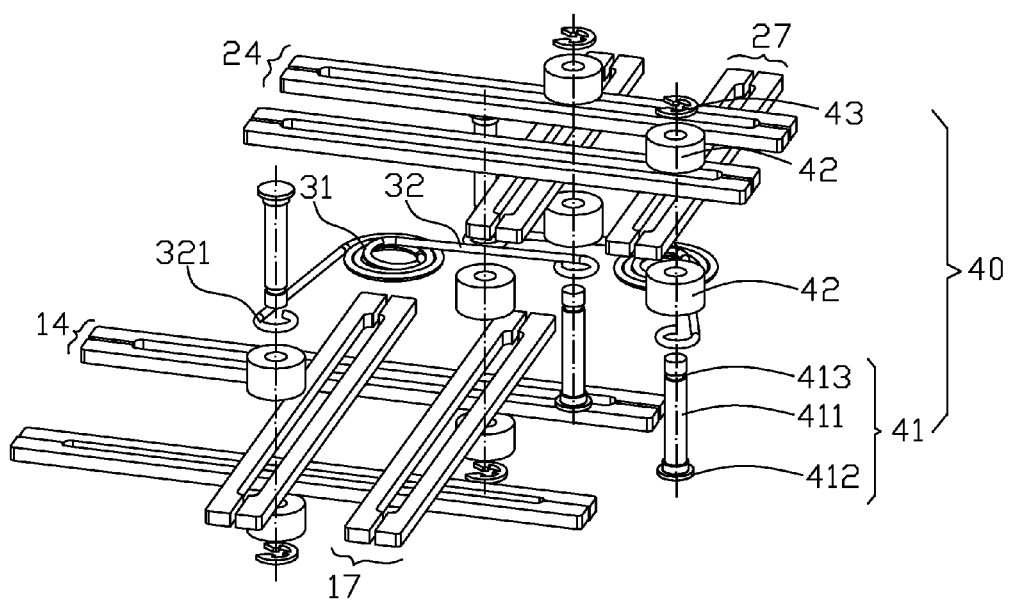
FIG. 3 is a partial exploded perspective view of the torsion spring test jig of FIG. 1 in an original status.

With reference to FIGS. 1-3, a torsion spring test jig 100 according to the present invention is shown. The torsion spring test jig 100 is adapted to assist one or more torsion springs 30 to show different elastic statuses so as to test the torsion springs 30 under the different elastic statuses. The torsion spring test jig 100 includes a bottom holder 10, a sliding element 20 and a plurality of hinge pin assemblies 40.

Figure 4:
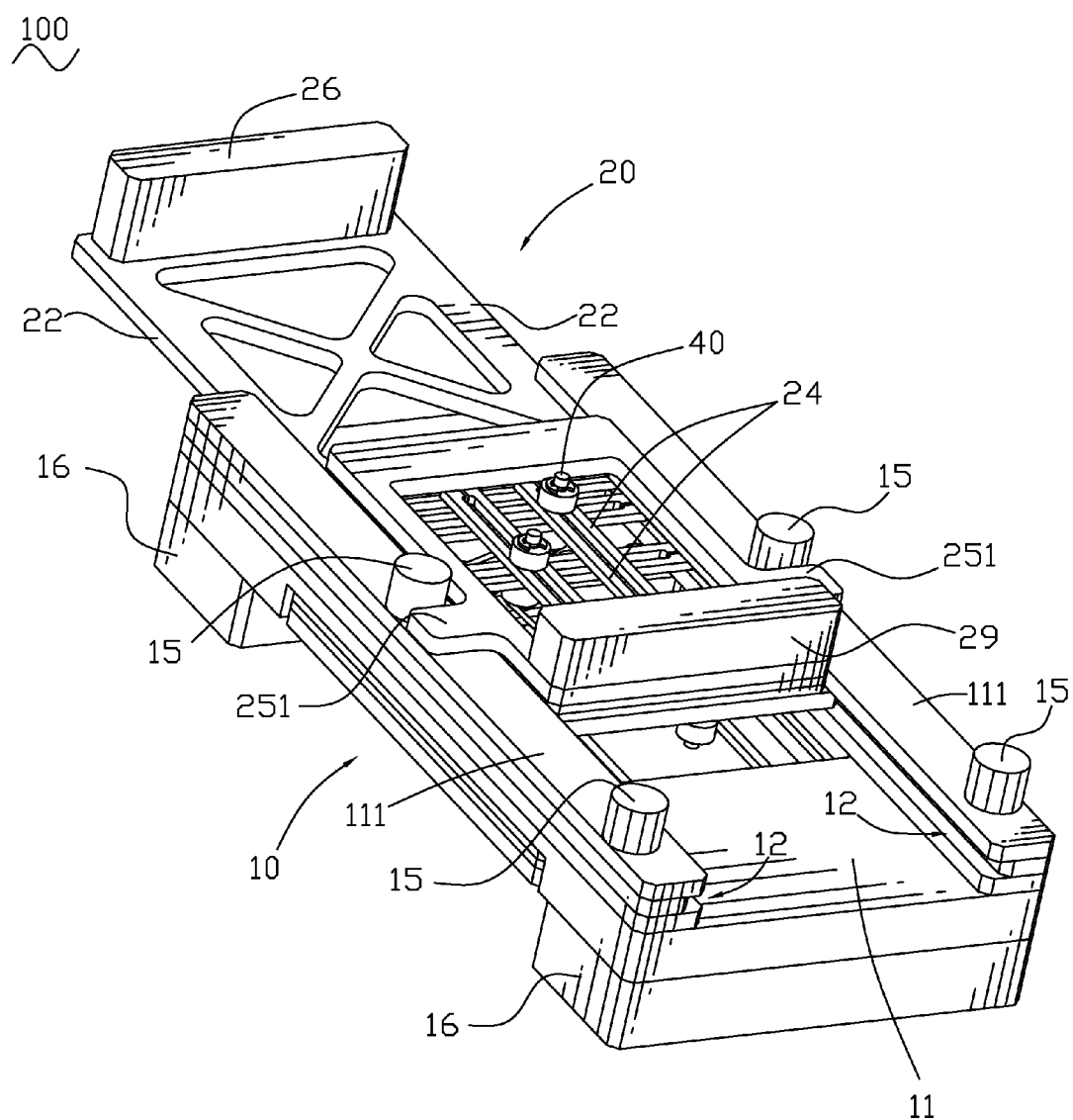
FIG. 4 is a perspective view of the torsion spring test jig of FIG. 1 in an opened status.
Figure 5:
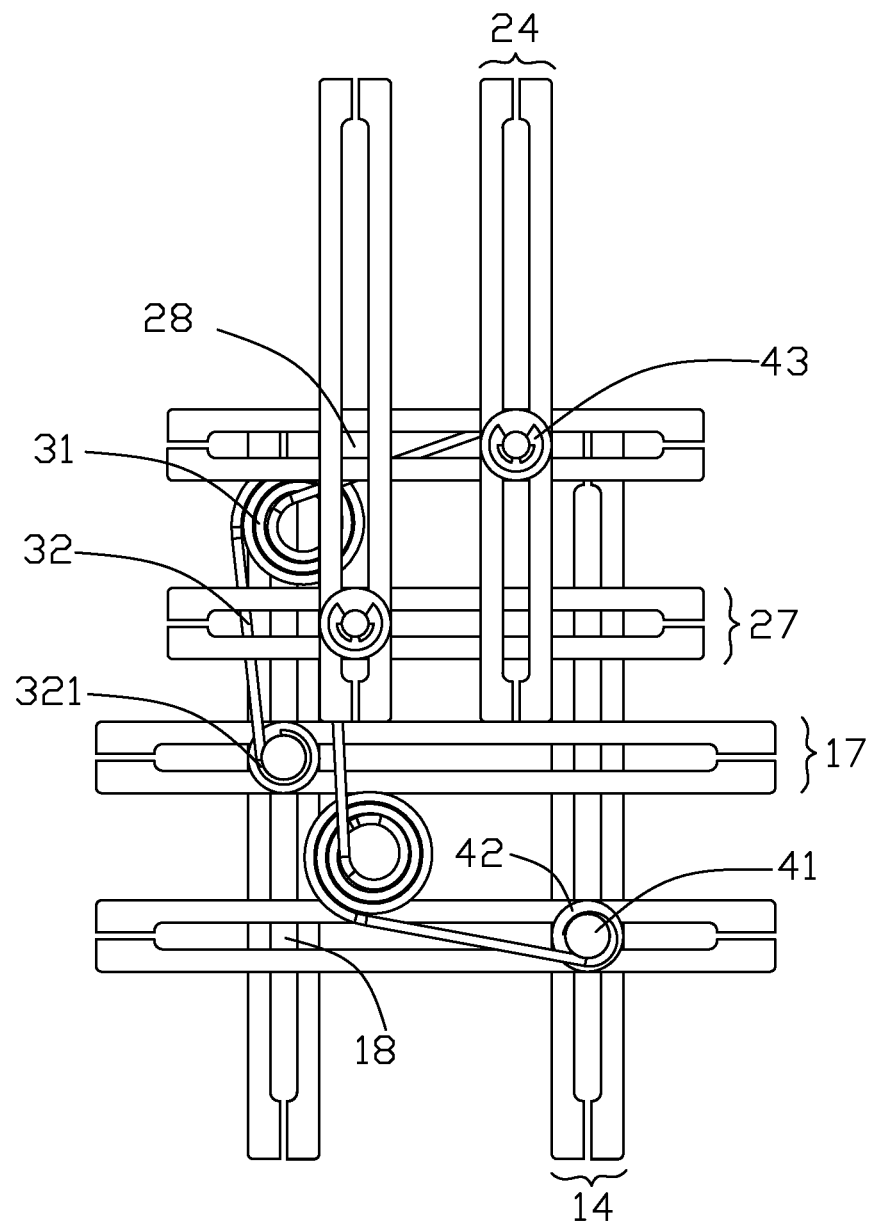
FIG. 5 is a partial top view of the torsion spring test jig of FIG. 3 in the original status.
Figure 6:
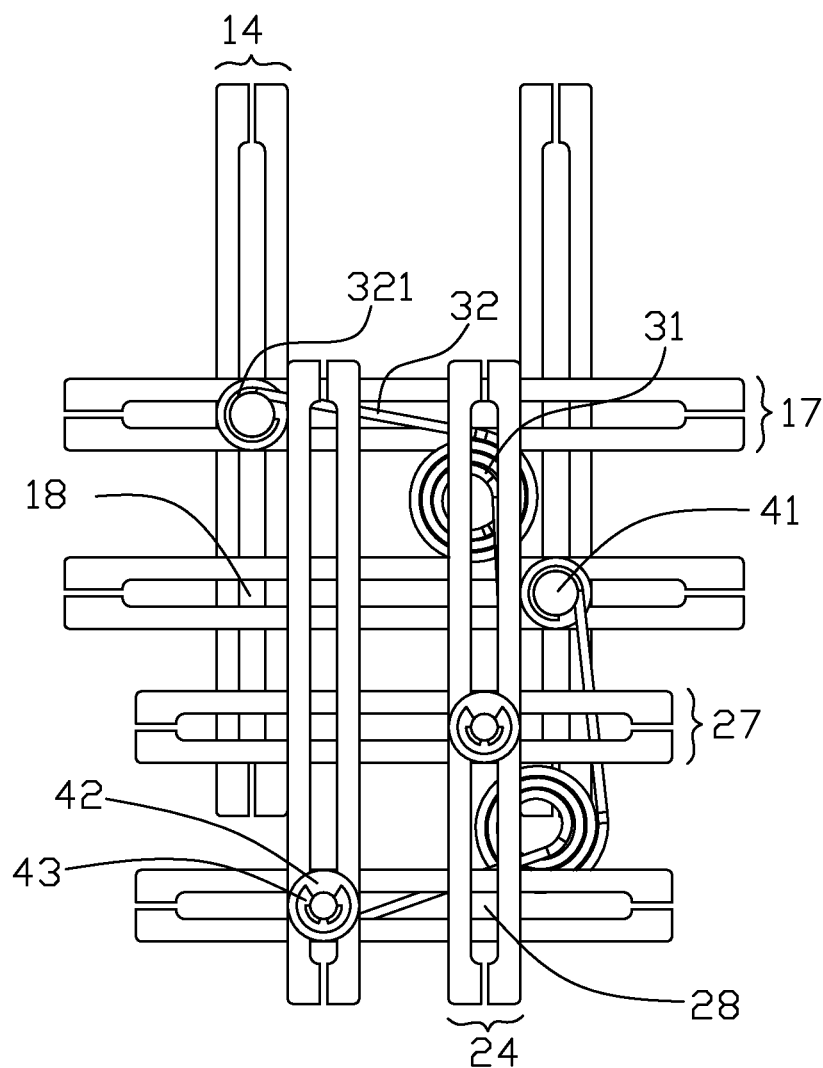
FIG. 6 is a partial top view of the torsion spring test jig of FIG. 4 in the opened status.

Referring to FIG. 1, FIG. 2 and FIG. 4, the bottom holder 10 has a base body 11 of rectangular shape. Two opposite sides of a top of the base body 11 protrude upward to form two elongated blocking portions 111 parallel to each other and each extending along a front-to-rear direction of the base body 11. Two inside surfaces of the blocking portions 111 are oppositely concaved inward to form two sliding grooves 12 each extending along the front-to-rear direction of the blocking portion 111. A top surface of each of the blocking portions 111 has two locating pillars 15 protruded upward from a front thereof and a substantial middle thereof, respectively. Two opposite ends of a bottom of the base body 11 protrude downward to form two support blocks 16. A middle of the base body 11 is cut off to define a rectangular first fastening frame 13. Two spaced first modulating fasteners 17 are slidably mounted in the first fastening frame 13 in parallel. Two spaced second modulating fasteners 14 are also slidably mounted in the first fastening frame 13 in parallel and perpendicularly positioned under the first modulating fasteners 17. In the embodiment, each of the second modulating fasteners 14 is positioned in the first fastening frame 13 along a direction parallel to the sliding grooves 12. The first modulating fastener 17 is made up of two parallel first strips 171 which are spaced from each other to define a first groove 172 therebetween. The second modulating fastener 14 has a similar shape to that of the first modulating fastener 17, and has two parallel second strips 141 spaced from each other to define a second groove 142 therebetween. Each intersection of the first groove 172 and the second groove 142 forms a first locating perforation 18 of which the position can be shifted with the relative movement between the first modulating fastener 17 and the second modulating fastener 14.

Referring to FIG. 1 and FIG. 2, the sliding element 20 has a base board 21 of rectangular shape, and a blocking board 25 mounted on a front of a top of the base board 21. Two opposite sides of the base board 21 are regarded as two sliding tracks 22 matching with the sliding grooves 12 of the bottom holder 10 in shape. A substantial middle of a front of the base board 21 is cut off to define a second fastening frame 23. A substantial middle of the blocking board 25 defines an opening 252. The opening 252 is wider than the second fastening frame 23 in length and width. Two spaced third modulating fasteners 24 are slidably mounted in the second fastening frame 23 in parallel. Two spaced fourth modulating fasteners 27 are also slidably mounted in the second fastening frame 23 in parallel and perpendicularly positioned under the third modulating fasteners 24. In the embodiment, each of the third modulating fasteners 24 is positioned in the second fastening frame 23 along a direction parallel to the sliding tracks 22. The third modulating fastener 24 is made up of two parallel third strips 241 which are spaced from each other to define a third groove 242 therebetween. The fourth modulating fastener 27 has a similar shape to that of the third modulating fastener 24, and has two parallel fourth strips 271 spaced from each other to define a fourth groove 272 therebetween. Each intersection of the third groove 242 and the fourth groove 272 forms a second locating perforation 28 of which the position can be shifted with the relative movement between the third modulating fastener 24 and the fourth modulating fastener 27. Fronts of two opposite sides of the blocking board 25 oppositely extend outward to form two blocking ears 251. A top of a rear end of the base board 21 protrudes upward to form a first pushing portion 26, and a top of a front end of the blocking board 25 protrudes upward to form a second pushing portion 29.

Referring to FIG. 3, the hinge pin assembly 40 includes a rivet 41, two ring-shaped cushion blocks 42 and a snap ring 43. The rivet 41 has a cylindrical pillar 411. One end edge of the cylindrical pillar 411 extends outward to form a ring-shaped blocking eave 412. The other end of the cylindrical pillar 411 is concaved inward to form a ring-shaped clipping groove 413.

Referring to FIG. 1, FIG. 2 and FIG. 4, when the torsion spring test jig 100 is assembled, the base board 21 of the sliding element 20 is slidably disposed over the bottom holder 10 to achieve a relative movement between the first locating perforation 18 and the second locating perforation 28. The base board 21 is located between the blocking portions 111, with the sliding tracks 22 being slidably inserted in the sliding grooves 12. The blocking board 25 is covered on the front of the top of the base board 21 with the third modulating fasteners 24 and the fourth modulating fasteners 27 being exposed from the opening 252 of the blocking board 25. Each of the blocking ears 25 is located on the blocking portion 111 and between the two locating pillars 15.

Referring to FIGS. 2-3, in this embodiment, there are two torsion springs 30 to be tested under different elastic statuses. Each of the torsion springs 30 includes an elastic loop 31 wound by a wire one circle after one circle. Two free ends of the elastic loop 31 are respectively extended outward along a tangent direction of an inner circle of the elastic loop 31 and an outer circle of the elastic loop 31 to form two elastic arms 32. Two free ends of the two elastic arms 32 are curved to from two opened fastening rings 321.

Referring to FIGS. 2-3, each of the torsion springs 30 should be assembled to the torsion spring test jig 100 before being tested. Specific steps of assembling the torsion springs 30 to the torsion spring test jig 100 are described as following. Firstly, move the first modulating fasteners 17 and the second modulating fasteners 14 to make sure a position of each first locating perforation 18. Secondly, put one of the opened fastening rings 321 of each torsion spring 30 around the end of the cylindrical pillar 411 adjacent to the blocking eave 412. Thirdly, the other end of the cylindrical pillar 411 with the clipping groove 413 opened therearound is inserted into one of the ring-shaped cushion blocks 42 to make the opened fastening ring 321 clipped between the cushion block 42 and the blocking eave 412. Fourthly, the other end of the cylindrical pillar 411 further passes through one of the first locating perforations 18. Fifthly, the other ring-shaped cushion block 42 is put around the other end of the cylindrical pillar 411 exposed from the first locating perforation 18. Lastly, the snap ring 43 is clipped in the clipping groove 413 to fasten the first strips 171 and the second strips 141 between the two cushion blocks 42. In a similar way, move the third modulating fasteners 24 and the fourth modulating fasteners 27 to make sure a position of each second locating perforation 28. Then repeat above-mentioned steps to fasten the other opened fastening ring 321 of the torsion spring 30 to the third modulating fastener 24 and the corresponding fourth modulating fastener 27 through the second locating perforation 28 by means of one hinge pin assembly 40. By now, the torsion spring 30 is positioned between the first and second modulating fasteners 17, 14, and between the third and fourth modulating fasteners 24, 27. The positions of the first locating perforation 18 and the second locating perforation 28 are made sure according to the shape of the torsion spring 30. After the torsion springs 30 are fastened to the torsion spring test jig 100, the sliding element 20 slides along the sliding grooves 12 of the bottom holder 10 to drive the torsion springs 30 to be flexibly expanded and contracted.

Referring to FIG. 1, FIG. 4, FIG. 5 and FIG. 6, specific steps of testing the torsion springs 30 are described as following. At first, the blocking ears 251 of the sliding element 20 resist against the two locating pillars 15 of the bottom holder 10 in the front of the blocking portions 111 to make the torsion spring test jig 100 at an original status, and each of the torsion springs 30 is at an original status accordingly. Then, push the second pushing portion 29 of the sliding element 20 rearward to make the sliding element 20 slide rearward with respect to the bottom holder 10, until the two blocking ears 251 are blocked against the two locating pillars 15 in the substantial middles of the blocking portions 111 to make the torsion spring test jig 100 at an opened status. At this time, the torsion spring 30 is at an expanded status accordingly. At last, push the first pushing portion 26 of the sliding element 20 frontward to make the sliding element 20 slide frontward with respect to the bottom holder 10, until the two blocking ears 251 are blocked against the two locating pillars 15 in the front of the blocking portions 111 again. At this time, the torsion spring test jig 100 returns the original status and the torsion spring 30 contracts to show the original status again. Repeat the above-mentioned steps to make the torsion springs 30 show different elastic statuses, so that different parameters of force condition and using life of the torsion springs 30 can be tested.

As described above, the torsion springs 30 are fastened between the first and second modulating fasteners 17, 14 of the bottom holder 10, and between the third and fourth modulating fasteners 24, 27 of the sliding element 20 of the torsion spring test jig 100 by means of the hinge pin assemblies 40. The sliding element 20 slides along the sliding grooves 12 of the bottom holder 10 to drive the torsion springs 30 to be flexibly expanded and contracted so as to show the different elastic statuses, so that different parameters of the force condition and the using life of the torsion springs 30 can be tested. Furthermore, the first modulating fastener 17, the second modulating fastener 14, the third modulating fastener 24 and the fourth modulating fastener 27 can be modulated to define different positions of the first and second perforations 18, 28 so as to meet varied needs of testing the torsion springs 30. So, the cost of testing the force condition and the using life of the torsion springs 30 is lowered and test efficiency is improved.

What is claimed is:

1. A torsion spring test jig adapted to assist a torsion spring to show different elastic statuses so as to test the torsion spring under the different elastic statuses, comprising:

a bottom holder having a base body, the base body defining a first fastening frame, a first modulating fastener being slidably mounted in the first fastening frame, and a second modulating fastener being slidably mounted in the first fastening frame and perpendicularly positioned under the first modulating fastener, the first modulating fastener having a first groove, and the second modulating fastener having a second groove extending perpendicularly to an extension direction of the first groove, each intersection of the first groove and the second groove forming a first locating perforation of which the position can be shifted with the relative movement between the first modulating fastener and the second modulating fastener;

a sliding element having a base board defining a second fastening frame, a third modulating fastener being slidably mounted in the second fastening frame, and a fourth modulating fastener being slidably mounted in the second fastening frame and perpendicularly positioned under the third modulating fastener, the third modulating fastener defining a third groove, and the fourth modulating fastener defining a fourth groove extending perpendicularly to the extension direction of the third groove, each intersection of the third groove and the fourth groove forming a second locating perforation of which the position can be shifted with the relative movement between the third modulating fastener and the fourth modulating fastener, the sliding element being slidably disposed over the bottom holder to achieve a relative movement between the first locating perforation and the second locating perforation; and a plurality of hinge pin assemblies, two free ends of the torsion spring being fastened to the first perforation and the second perforation respectively by means of the hinge pin assemblies to mount the torsion spring between the first and second modulating fasteners, and between the third and fourth modulating fasteners.

2. The torsion spring test jig as claimed in claim 1, wherein the sliding element further includes a blocking board mounted on a top of the base board, the blocking board defines an opening wider than the second fastening frame in length and width for exposing the third modulating fastener and the fourth modulating fastener therefrom, two opposite sides of the blocking board oppositely extend sideward to form two blocking ears, each side of a top of the base body protrudes upward to form a blocking portion with two locating pillars protruded upward thereon and spaced from each other along the slide direction of the sliding element, the base board of the sliding element is slidably mounted between the blocking portions with each blocking ear slidably positioned between the two locating pillars to restrain the relative movement between the sliding element and the bottom holder.

3. The torsion spring test jig as claimed in claim 2, wherein one end of the base board protrudes upward to form a first pushing portion, and one end of the blocking board far away from the first pushing portion protrudes upward to form a second pushing portion, the first and second pushing portions can be pushed to drive the sliding element to slide with respect to the bottom holder.

4. The torsion spring test jig as claimed in claim 1, wherein two opposite sides of the base board protrude upward to form two blocking portions of which two inside surfaces are oppositely concaved inward to form two sliding grooves each extending along the slide direction of the sliding element, the base board of the bottom holder is slidably mounted between the blocking portions with two opposite sides of the base board regarded as two sliding tracks slidably inserted in the sliding grooves.

5. The torsion spring test jig as claimed in claim 1, wherein each modulating fastener is made up of two parallel strips which are spaced from each other to define the groove therebetween.

6. The torsion spring test jig as claimed in claim 1, wherein the torsion spring has two opened fastening ring at two free ends thereof, the hinge pin assembly includes a rivet, two ring-shaped cushion blocks and a snap ring, the rivet has a cylindrical pillar, one end edge of the cylindrical pillar extends outward to form a ring-shaped blocking eave, the other end of the cylindrical pillar is concaved inward to form a ring-shaped clipping groove, the other end of the cylindrical pillar successively passes through one fastening ring of the torsion spring, one of the cushion blocks, the locating perforation and the other cushion block, and then the snap ring is clipped in the clipping groove to secure the fastening ring with the hinge pin assembly and between the cushion block and the blocking eave.

* * * * *